(12) United States Patent
Setoodeh et al.

(10) Patent No.: US 9,173,444 B2
(45) Date of Patent: Nov. 3, 2015

(54) SIZING WHEEL FOR MEDICAL UNDERGARMENTS

(71) Applicant: Medline Industries, Inc., Mundelein, IL (US)

(72) Inventors: Amin Setoodeh, Kildeer, IL (US); Robert Irving, Carol Stream, IL (US)

(73) Assignee: Medline Industries, Inc., Mundelein, IL (US)

( * ) Notice: Subject to any disclaimer, the term of this patent is extended or adjusted under 35 U.S.C. 154(b) by 188 days.

(21) Appl. No.: 13/717,391

(22) Filed: Dec. 17, 2012

(65) Prior Publication Data

US 2013/0152847 A1 Jun. 20, 2013

Related U.S. Application Data

(60) Provisional application No. 61/577,333, filed on Dec. 19, 2011.

(51) Int. Cl.
| | | |
|---|---|---|
| *G01G 1/00* | (2006.01) | |
| *A61F 13/84* | (2006.01) | |
| *A41H 1/00* | (2006.01) | |
| *G06G 1/00* | (2006.01) | |

(52) U.S. Cl.
CPC ............ *A41H 1/00* (2013.01); *A61F 13/84* (2013.01); *G06G 1/00* (2013.01); *G06G 1/001* (2013.01); *A61F 2013/8473* (2013.01)

(58) Field of Classification Search
CPC ........... G06G 1/00; G06G 1/001; A41H 1/00; A61F 13/84; A61F 2013/8473
USPC ................. 33/1 SB, 512, 1 SD; 235/78 R
See application file for complete search history.

(56) References Cited

U.S. PATENT DOCUMENTS

| | | | | | |
|---|---|---|---|---|---|
| 1,922,465 | A | * | 8/1933 | Woodward | 235/78 R |
| 2,328,881 | A | * | 9/1943 | Saunders | 235/78 R |
| 3,279,695 | A | * | 10/1966 | Krause | 235/78 N |
| 3,627,200 | A | * | 12/1971 | Sadler | 235/88 G |
| 3,718,519 | A | * | 2/1973 | Montgomery | 156/250 |
| 3,721,007 | A | * | 3/1973 | Banner | 33/1 SD |
| 4,026,463 | A | * | 5/1977 | Betzler | 235/88 R |
| 4,048,477 | A | * | 9/1977 | Hungerford | 235/88 R |
| 4,399,353 | A | * | 8/1983 | Adkins et al. | 235/78 R |
| 4,754,125 | A | * | 6/1988 | Penn | 235/88 R |
| 4,797,539 | A | * | 1/1989 | Forest | 235/85 R |
| 4,918,412 | A | * | 4/1990 | Churchill | 235/88 R |
| 5,010,656 | A | * | 4/1991 | Broselow | 33/759 |
| 5,017,762 | A | * | 5/1991 | Diamond | 235/78 R |
| 5,374,461 | A | * | 12/1994 | Bromberg | 428/43 |
| 5,398,418 | A | * | 3/1995 | Jones | 33/1 SD |
| 5,412,874 | A | * | 5/1995 | Madden | 33/1 SB |

(Continued)

*Primary Examiner* — Christopher Fulton
(74) *Attorney, Agent, or Firm* — Philip H. Burrus, IV

(57) ABSTRACT

A device (100) for determining an appropriately sized medical undergarment for a wearer includes a housing (101) and a wheel (102). A first body mass index factor alignment indicator (108) can be aligned with a first body mass index factor, such as weight of a wearer, thereby revealing color coded symbols (109) aligned with a plurality of second body mass factor alignment indicators (110). A user selects the appropriate size by determining which color is aligned with a second body mass factor alignment indicator of the wearer. An optional second side (205) of the device (100) can be used to determine an appropriate type of medical undergarment based upon urinary output, wearer mobility, or combinations thereof.

20 Claims, 7 Drawing Sheets

(56) References Cited

U.S. PATENT DOCUMENTS

| | | | |
|---|---|---|---|
| 6,265,651 B1 * | 7/2001 | Landtroop | 84/471 R |
| 6,311,403 B1 | 11/2001 | Macrini | |
| 6,484,932 B1 * | 11/2002 | Kinney et al. | 235/73 |
| 6,488,202 B1 | 12/2002 | Seitz et al. | |
| 6,648,219 B1 * | 11/2003 | Daunell | 235/78 R |
| 7,337,946 B2 * | 3/2008 | Belton | 235/89 R |

* cited by examiner

US 9,173,444 B2

SIZING WHEEL FOR MEDICAL UNDERGARMENTS

CROSS REFERENCE TO PRIOR APPLICATIONS

This application claims priority and benefit under 35 U.S.C. §119(e) from U.S. Provisional Application No. 61/577,333, filed Dec. 19, 2011.

BACKGROUND

1. Technical Field

This invention relates generally to a tool for determining an appropriately designed medical undergarment, and more particularly to a rotational sizing wheel with which both size and type of medical undergarment can be determined from wearer measurement, urinary output, mobility, and combinations thereof.

2. Background Art

Many people suffer incontinence issues. Sometimes the symptoms are temporary, such as from medical procedures, medications, or temporary mobility issues. Other times the symptoms are longer lasting. To accommodate such issues, manufacturers have developed absorbent medical undergarments. A user wears these undergarments, which can be configured as scoop-shaped pads, briefs, or sheet-like devices, to absorb inadvertent waste discharge.

As people come in many different shapes, manufacturers have developed different sized undergarments. Further, some undergarments are designed for large amounts of urinary output while others are designed for only modest levels of output. One problem associated with the many sizes and types of undergarments is selecting the proper size and type of undergarment for a particular patient.

For example, when a patient is hospitalized and suffers from temporary incontinence issues, it can sometimes be difficult for a nurse to move the patient sufficiently to take proper measurements to determine the appropriately sized undergarment. Consequently, the patient may be fitted with an improperly sized undergarment, which can result in leakage, chafing, diaper rash, skin irritation, and reduced dignity for the user.

There is thus a need for a device and method suitable for quickly and conveniently determining an appropriately sized undergarment for a wearer.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
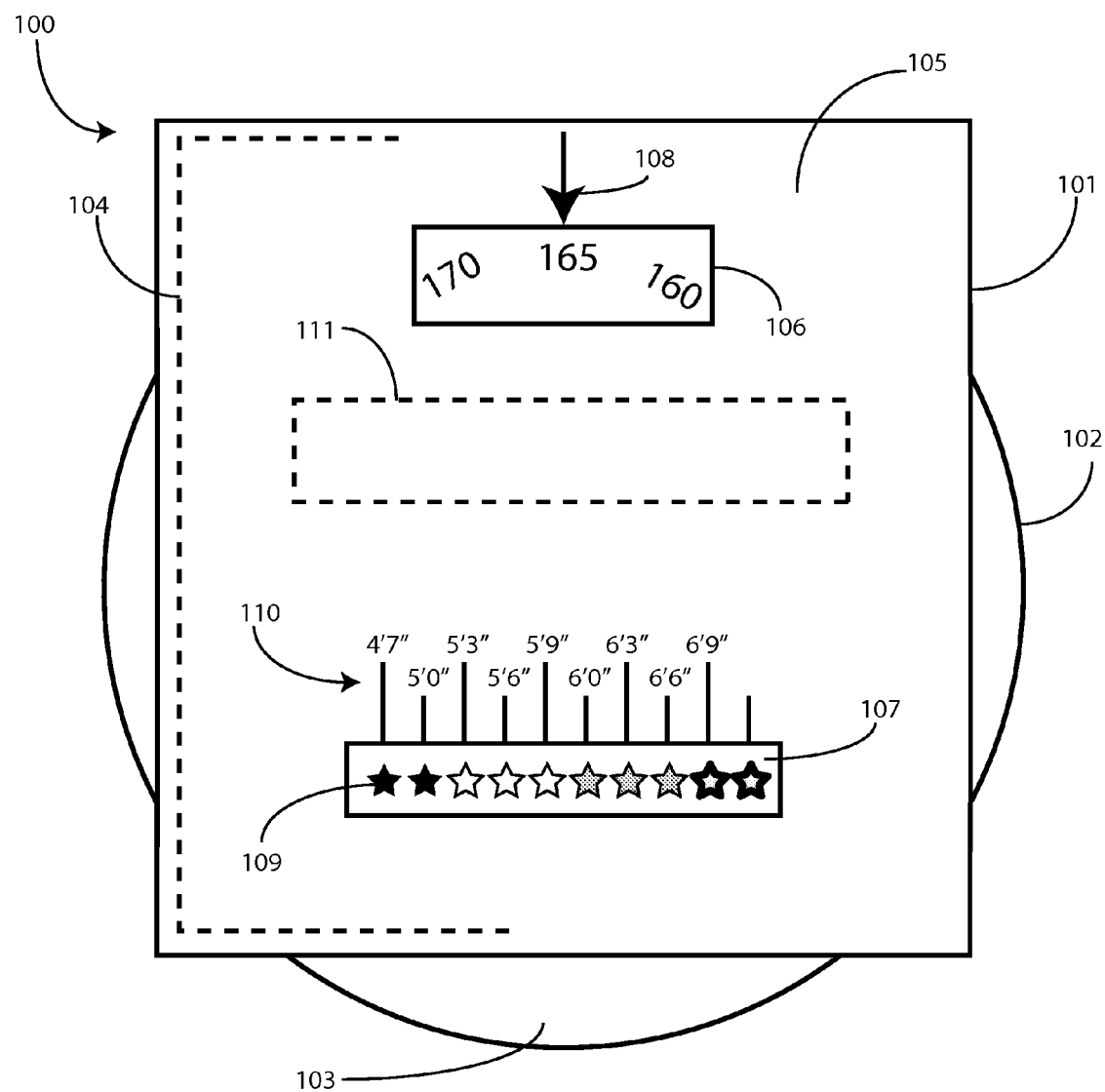
FIG. 1 illustrates one device for determining an appropriately sized medical undergarment in accordance with embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the present invention provide convenient, easy to use, easy to carry in a pocket tools to help health care services providers, such as nurses or nurse aides in long-term care facilities or hospitals, select an appropriate size of a medical undergarment. Some embodiments help the healthcare services provider determine an appropriate type of medical undergarment as well. For example, in one embodiment, by entering a wearer measurement, which may be a body mass index parameter such as height or weight, the health care service provider will be able to select a more appropriate incontinence management product than they would with visual inspection alone. Further, in one embodiment, the health care services provider may also input information relating to urinary output, thereby enabling them to determine an appropriate type of incontinence product from a line.

Some medical undergarment manufacturers provide complex, computer-based programs that attempt to provide an indication of what size undergarment is appropriate for a particular patient. However, these computer-based programs suffer from several limitations. First, the computer-based format requires that a health care services provider have access to both a computer and the Internet. In a hospital environment, this is frequently not the case.

Second, even if a computer and Internet access is available, these prior art systems require the health care services provider to take several measurements, write them down, leave the patient to access the computer, determine which undergarment might be appropriate, and so forth. There is frequently no time available to do this when treating incontinent patients.

Embodiments of the present invention offer advantages to these computer based programs in that some embodiments of the present invention are configured as easy to use sizing wheels that can be carried from patient to patient. Further, in one embodiment, the sizing wheel is less than five and one half by six inches, so as to be easily stowed in a small scrub pocket. Further, in one embodiment, the sizing wheel is configured with a hanging aperture such that it can be hung on hooks. By way of example, the sizing wheel may be hung on the hook of a store room such that a health care services provider carrying a chart with the patient's measurements can instantly select an appropriate sized undergarment.

Next, in one embodiment the sizing wheel is color-coded so as to correspond to a particular size and/or type of medical undergarment. For example, some medical undergarment manufactures, such as Medline, Inc. of Mundelein, Ill., manufacture various sizes and absorbencies of medical undergarments with color-coded packaging. Embodiments of the present invention provide the health care services provider with a simple visual method of associating a selected medical undergarment on the tool with an actual medical undergarment in a stock room.

Figure 2:
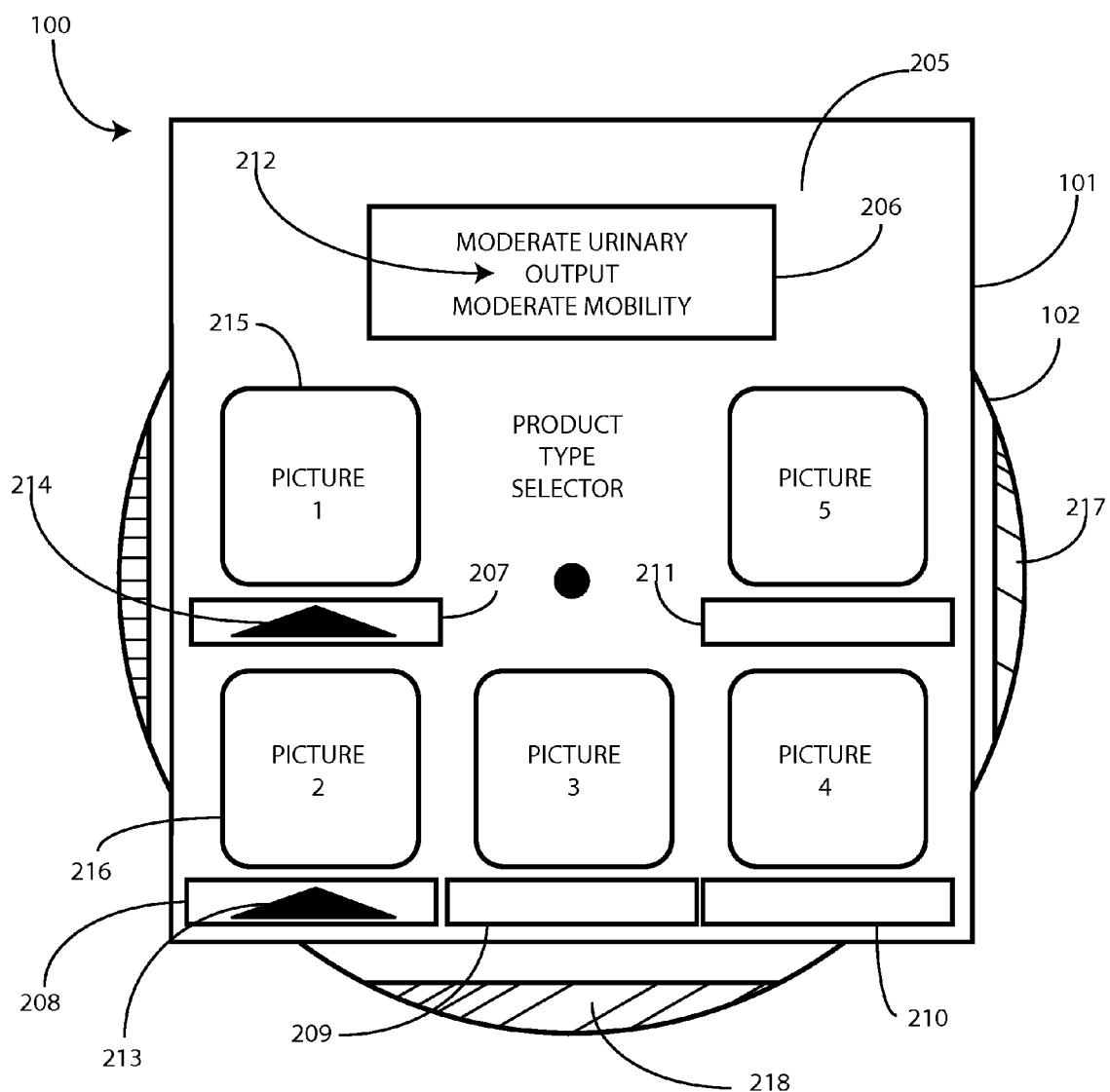
FIG. 2 illustrates one device for determining an appropriately sized medical undergarment in accordance with embodiments of the invention.

Turning now to FIGS. 1 and 2, illustrated therein is one embodiment of a device 100 for determining an appropriately sized medical undergarment for a wearer in accordance with the invention. The device 100 of FIG. 1 is configured as a two-sided tool having a housing 101 and a wheel 102. The wheel 102 is coupled to the housing 101 so as to be rotatably moved within the housing 101. In one embodiment, at least portions 103 of the wheel 102 are accessible by a user about a perimeter 104 of the housing 101.

The housing 101, in one embodiment, includes a first side 105 and a second side 205. In one embodiment, each side 105,205 can include one or more apertures 106,107,206,207, 208,209,210,211 through which information disposed on the wheel 102 can be seen. For discussion purposes herein, the illustrative embodiment will be that of a wheel 102 disposed within a housing 101, which the housing 101 including apertures through which information disposed on the wheel 102 can be seen. It will be obvious to those of ordinary skill in the art having the benefit of this disclosure, however, that the invention is not so limited. Embodiments of the invention could be configured such that the housing is disposed along side or within the wheel, for example. In such an embodiment, the wheel may include apertures through which information disposed on the housing could be seen. Alternatively, both the wheel and housing could have apertures. In another embodiment, pointers on the perimeter of either the wheel or housing could be used instead of aperture windows. The embodiment of FIGS. 1 and 2 is but one embodiment used for illustration purposes only.

Beginning with the first side 105, in one embodiment a first body mass index factor alignment indicator 108 is disposed on the housing 101 near to or adjacent to a first aperture 106. In one embodiment, the first body mass index factor alignment indicator 108 is used to point or become aligned with body mass index factors disposed on the wheel 102 that are visible in the first aperture 106 when the wheel is rotated. Examples of factors suitable for use as the first body mass index factor include height and weight. In one embodiment, weight is used as the first body mass index factor. In such an embodiment, a health care services provider rotates the wheel 102, thereby causing various weights printed or otherwise disposed on the wheel 102 to become visible in the first aperture 106. The health care services provider inputs a patient's weight into the device by rotating the wheel 102 until the patient's weight is aligned with the first body mass index factor alignment indicator 108.

When this is done, i.e., when the first body mass index factor alignment indicator 108 is aligned with an appropriate first body mass index factor, color coded symbols 109, disposed on the wheel 102, become visible through a second aperture 107. In one embodiment, the housing 101 includes a plurality of second body mass factor alignment indicators 110 disposed thereon near to or adjacent with the second aperture 107. Where, for example, the first body mass index factor is weight, the second body mass index factor can be height. Thus, the plurality of second body mass factor alignment indicators 110 can comprise a plurality of height measurements. The opposite can be true as well. Where the first body mass index factor is height, the plurality of second body mass factor alignment indicators 110 can comprise a plurality of weights.

When the plurality of color-coded symbols 109 are revealed within the second aperture 107, each aligns with one of the plurality of second body mass factor alignment indicators 110. This indicates an appropriately sized medical undergarment for a patient based upon two body mass index factors. As each of the plurality of second body mass factor alignment indicators 110 corresponds to a particular color coded symbol, the health care services provider simply selects the appropriate size by determining which color is aligned with a second body mass factor alignment indicator of the patient.

The various color codes can be explained in a legend 111 disposed on the housing 101. For example, a first color can correspond to a first size undergarment, a second color can correspond to a second size undergarment, and so forth. Note that while the housing 101 includes a plurality of second body mass factor alignment indicators 110 disposed about a single aperture, the second aperture 107, it will be clear to those of ordinary skill in the art having the benefit of this disclosure that embodiments of the invention are not so limited. The first side 105 of the housing 101 could, for example, include a plurality of apertures, each being aligned with one, two, or three of the plurality of second body mass factor alignment indicators 110 as well.

Turning to the second side 205, in one embodiment this side can be used to determine an appropriate type of medical undergarment based upon urinary output, wearer mobility, or combinations thereof. In the illustrative embodiment of FIGS. 1 and 2, the wheel 102 includes descriptions 212 of urinary output and wearer mobility. The health care services provider inputs an appropriate description by rotating the wheel 102 until a description corresponding to a particular patient appears in a first aperture 206.

Note that while a combined urinary output and wearer mobility appears in a single aperture in the illustrative embodiment of FIG. 2, it will be clear to those of ordinary skill in the art that embodiments of the invention are not so limited. For example, one device may utilize only urinary output, which appears in a single window. Another device may utilize only wearer mobility, which appears in a single window. Alternatively, urinary output could appear in a first aperture or window, while wearer mobility appears in a second window, and so forth.

In one embodiment, the second side 205 of the housing 101 can include information corresponding to one or more types of medical undergarments disposed thereon. For example, in one embodiment, the information can include model names or types of medical undergarments. In another embodiment, the information can include manufacturer and/or part number information corresponding to the various types of medical undergarments. In FIG. 2, the information is shown as pictorial representations of medical undergarments, such as pictorial representations 215,216.

In the illustrative embodiment of FIG. 2, when the appropriate description 212 of urinary output and wearer mobility is aligned so as to appear in the first aperture 206, corresponding pointers 213,214 are revealed in other apertures, e.g., apertures 207,208. These one or more pointers 213,214 point to one or more pictorial representations of the medical undergarments. In FIG. 2, for example, pointer 214 points to pictorial representation 215, while pointer 213 points to pictorial representation 216. This indicates that the medical undergarments corresponding to pictorial representations 215,216 are appropriate for the wearer based upon the selected urinary output and mobility, while the other pictorial representations are not.

In addition to pointers 213,214, the outer portions of the wheel 102 may be color-coded as well. For example, where the product shown in the selected pictorial representations 215,216 are color-coded, or are shipped in color-coded packaging, colors 217,218 on outer portions of the wheel 102 may become visible when those products are indicated by the pointer 213,214.

Thus, with the device 100 of FIGS. 1 and 2, a healthcare services provider is able, for example, to look at the first side 105 of the device 100 and turn the wheel 102 to select a person's weight. By reading a color of a corresponding color-coded symbol 109 appearing in a second aperture 107 aligned with the wearer's height, an indication of an appropriate size of medical undergarment is obtained. By turning to the second side 205 of the device, the health care services provider may input the wearer's urinary output and mobility. Pointers 213,214 or colors 217,218, or combinations thereof then indicate a particular medical undergarment, which in one embodiment comprises a recommended incontinence management product.

The device 100 of FIGS. 1 and 2 offers a simplified product selection and sizing tool that can enable a health care services provider or other user to select an appropriate absorbent disposable product based on a wearer's level of incontinence, which may include mobility and urinary output, as well as the wearer's body mass index factors of height and weight. The device 100 is a simple, functional tool that can easily be placed in a scrub pocket, or that can be hooked on a cart or in a storeroom. Further, the device 100 does not require Internet or computer access to obtain customized undergarment information.

Figure 3:
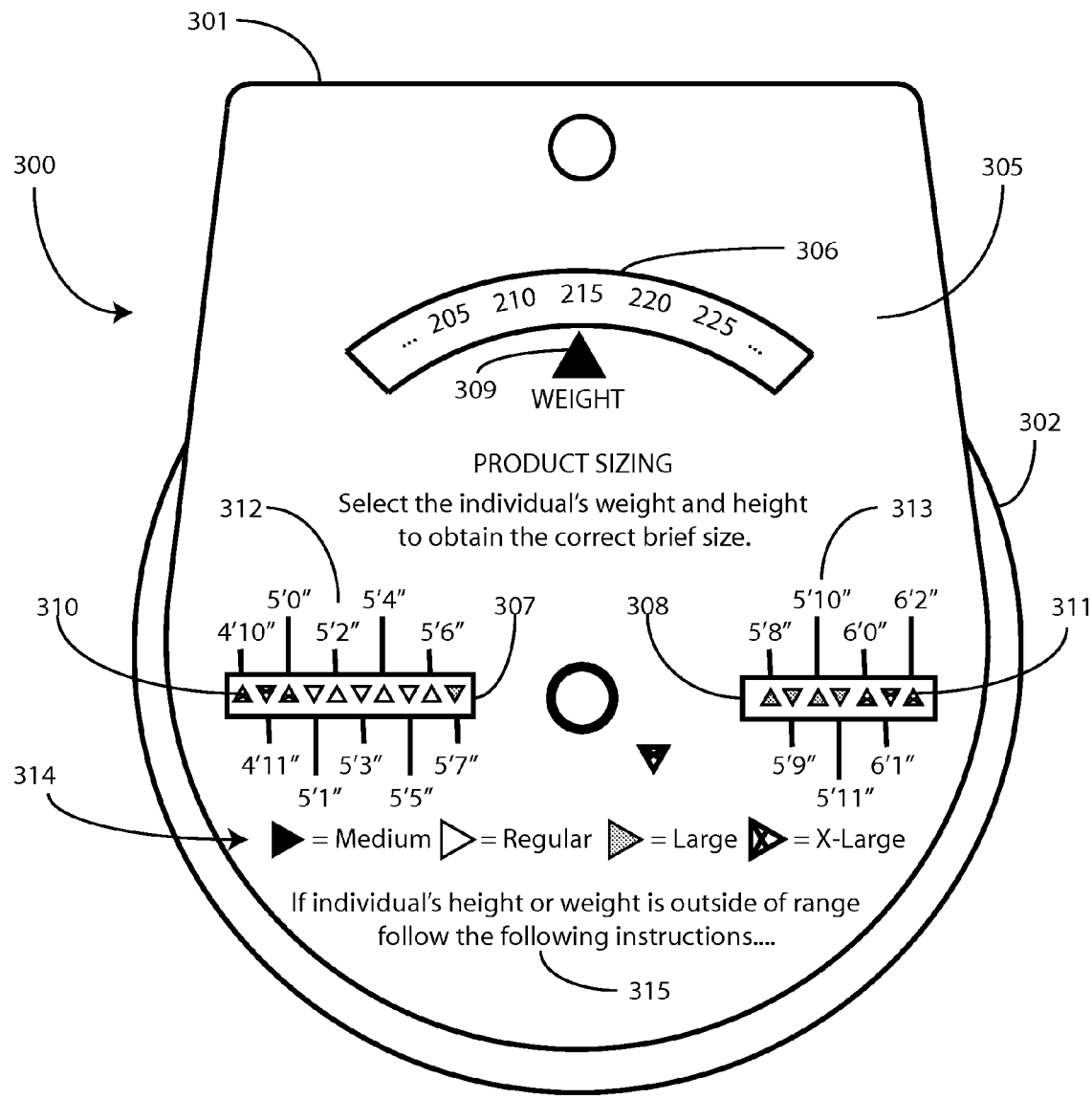
FIG. 3 illustrates another device for determining an appropriately sized medical undergarment in accordance with embodiments of the invention.
Figure 4:
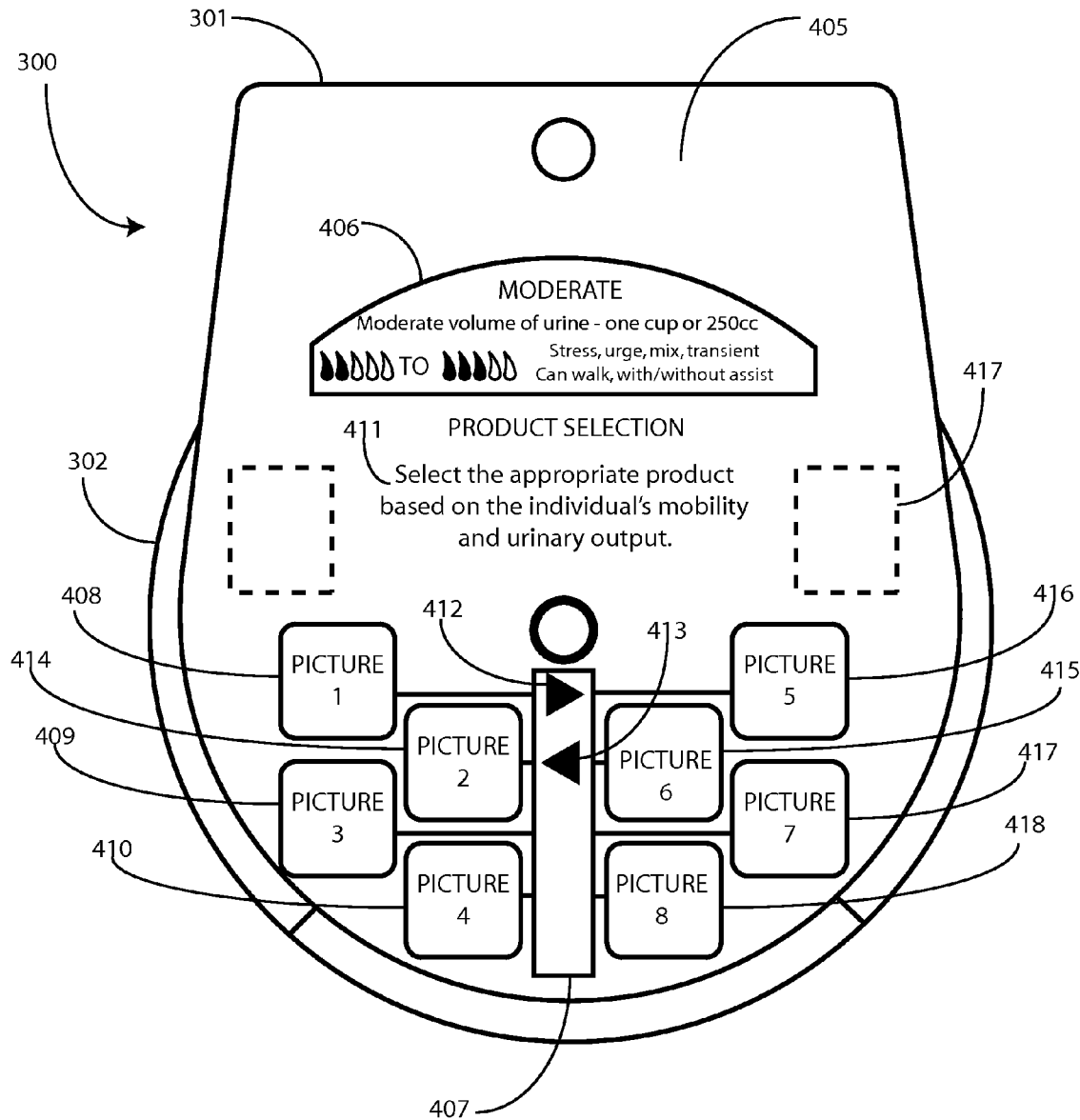
FIG. 4 illustrates another device for determining an appropriately sized medical undergarment in accordance with embodiments of the invention.

Turning now to FIGS. 3 and 4, illustrated therein is another device 300 suitable for determining an appropriately sized medical undergarment in accordance with embodiments of the invention. The device 300 of FIGS. 3 and 4 includes an exterior member 301 having a first side 305 and a second side 405. In one embodiment, the first side 305 and second side 405 are different colors. For example, the first side 305 may be green, while the second side 405 is purple. In the illustrative embodiment of FIGS. 3 and 4, each of the first side 305 and second side 405 defines at least two apertures. For example, side 305 defines apertures 306,307,308, while side 405 defines apertures 406,407.

An inner member 302 is coupled to the exterior member 301 so as to be pivotally movable within the exterior member 301. In this illustrative embodiment, portions of the inner member 302 are exposed outside the perimeter of the exterior member 301. A user can thus access these portions to cause pivotal movement of the inner member 302.

A first wearer measurement alignment indicator 309 is disposed on the first side 305 of the exterior member 301. In one embodiment, the first wearer measurement alignment indicator 309 can be disposed adjacent to a first aperture 306. In the embodiment of FIG. 3, the first wearer measurement is that of weight. Thus, the first wearer measurement alignment indicator 309 includes a descriptor that says "weight." Instructions can be printed therebeneath. In this illustrative embodiment, the instructions read, "Select the individual's weight and height to obtain the correct brief size." A user then grasps the outer portions of the inner member 302 and rotates the inner member 302 relative to the exterior member 301 until the wearer's weight is aligned with the first wearer measurement alignment indicator 309.

When this occurs, a corresponding plurality of color-coded sizing symbols 310,311 appear in at least one aperture. This occurs because a plurality of color-coded sizing symbols are disposed about the inner member 302 so as to be at least partially visible through aperture 306, with each color representing a different size of medical undergarment. Various colors and combinations of colors can be used for the symbols. In one embodiment, the plurality of color-coded symbols comprises combinations of symbols having one of four colors, with the four colors corresponding to four sizes of medical undergarments.

The various colors can be explained, graphically or textually, with a legend 314 disposed on the exterior member 301. For example, a color of white may correspond to a medium medical undergarment, while a color of purple may correspond to a regular medical undergarment. Similarly, a color of blue may correspond to a large undergarment, while a color of grey may correspond to an extra-large undergarment.

A plurality of second wearer measurement alignment indicators 312,313 can be disposed on the first side 305 of the exterior member 301 adjacent to one or more apertures 307, 308. In one embodiment where the first wearer measurement is weight, the second wearer measurement can be height, as shown in FIG. 3.

In the illustrative embodiment of FIG. 3, some of the plurality of second wearer measurement alignment indicators 312 is disposed adjacent to aperture 307, while others of the plurality of second wearer measurement alignment indicators 313 are disposed adjacent to aperture 308. Said differently, while one plurality of second wearer measurement alignment indicators 312 are disposed by a second aperture 307 of the first side 305 of the exterior member 301, a second plurality of second wearer measurement alignment indicators 313 can be disposed on the exterior member 301 adjacent to a third aperture 308. Illustrating by example, the some of the plurality of second wearer measurement alignment indicators 312 comprise height indicators ranging from four feet, ten inches tall to five feet, seven inches tall. The others of the plurality of second wearer measurement alignment indicators 313 comprise height indicators ranging from five feet, eight inches tall to six feet, two inches tall. These ranges, number of apertures, and arrangement are illustrative only.

When the first wearer measurement is aligned with the first wearer measurement alignment indicator 309, the corresponding plurality of color-coded sizing symbols 310,311 become visibly aligned with the plurality of second wearer measurement alignment indicators 312,313, thereby indicating the appropriately sized medical undergarment for each of the plurality of second wearer measurement alignment indicators. Where two apertures 307,308 are used, a first corresponding plurality of color-coded sizing symbols 310 become visibly aligned with the plurality of second wearer measurement alignment indicators 312, and a second corresponding plurality of color-coded sizing symbols 311 become visibly aligned with the second plurality of second wearer measurement alignment indicators 313, thereby indicating a first set of appropriately sized medical undergarments for each of the plurality of second wearer measurement alignment indicators 312 and a second set of appropriately sized medical undergarments for each of the second plurality of second wearer measurement alignment indicators 313. By selecting the color aligned with the wearer's height, the user may quickly and easily select an appropriately sized undergarment.

In one embodiment, the plurality of color-coded sizing symbols 310,311 are each configured as triangles, so as to point to one of a plurality of second wearer measurement alignment indicators 312,313. Where, for example, the plurality of second wearer measurement alignment indicators 312,313 are disposed on multiple sides of each aperture 307, 308, some of the triangles may point to a first side, while others point to a second side, as shown in FIG. 3.

In one embodiment, the first side 305 of the exterior member 301 can include other information as well. For example, in one embodiment, the first side 305 includes instructions 315 for selecting an appropriately sized undergarment when one of the wearer's measurements is outside of the ranges included in the device 300.

Turning now to the second side 405, in one embodiment it includes pictorial representations 408,409,410 of a plurality of medical undergarments disposed on the exterior member 301 adjacent to aperture 407. In one embodiment, the inner member 302 comprises wearer discharge information thereon so as to be visible through aperture 406. This wearer discharge information can include urinary output information, wearer mobility information, or combinations thereof.

Instructions 411 for using the second side 405 may be included as well. For example, in one embodiment the instructions 411 can read, "Select the appropriate product based on the individual's mobility and urinary output." A user may then rotate the inner member 302 relative to the exterior member 301 so as to align the proper discharge information to appear in aperture 406.

When a user-selected wearer discharge description is visible within aperture 406, one or more pointers 412,413 become visible in aperture 407. The one or more pointers 412,413 identify which of the plurality of medical undergarments are appropriate by pointing to each corresponding pictorial representation. In one embodiment, each pictorial representation can comprise a color-coding. Correspondingly, each pointer appearing in aperture 407 can be color coded to make identification of a particular product even simpler.

By way of example, in the illustrative embodiment of FIG. 4, pictorial representation 408 corresponds to a light urinary output, female undergarment with a yellow color code, while pictorial representation 409 corresponds to a heavy urinary output undergarment with a blue color code. Pictorial representation 410 corresponds to a heavy plus stool undergarment with a purple color code, while pictorial representation 414 corresponds to a moderate urinary output undergarment with a green color code. Pictorial representations 415,417,418 correspond to a heavy urinary output undergarment with a blue color code, while pictorial representation 416 corresponds to a light-to-moderate urinary output undergarment with a yellow and green color code.

Figure 5:
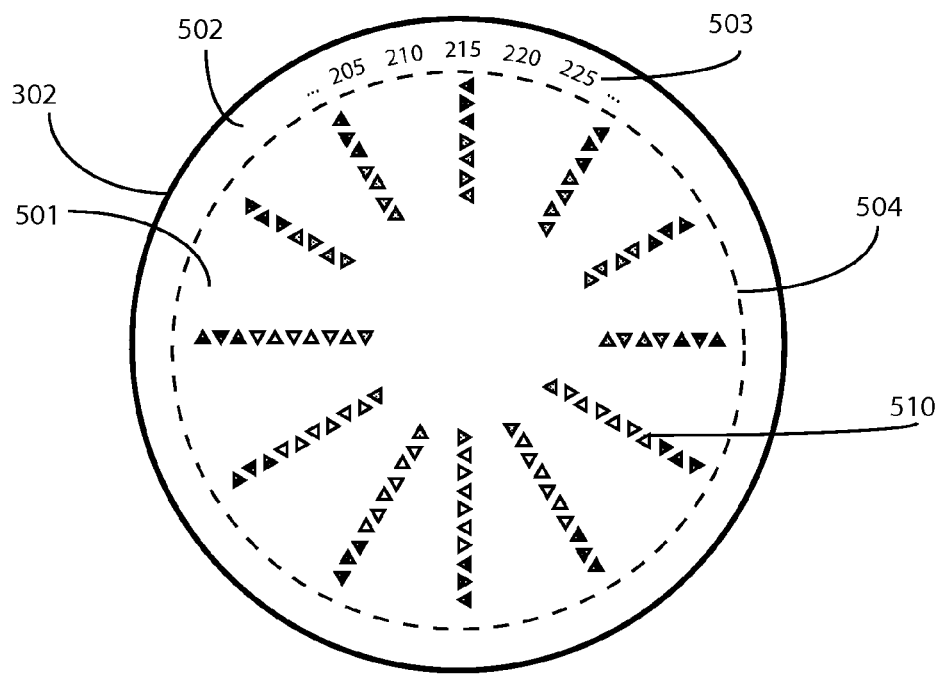
FIG. 5 illustrates one embodiment of a wheel in accordance with embodiments of the invention.
Figure 6:
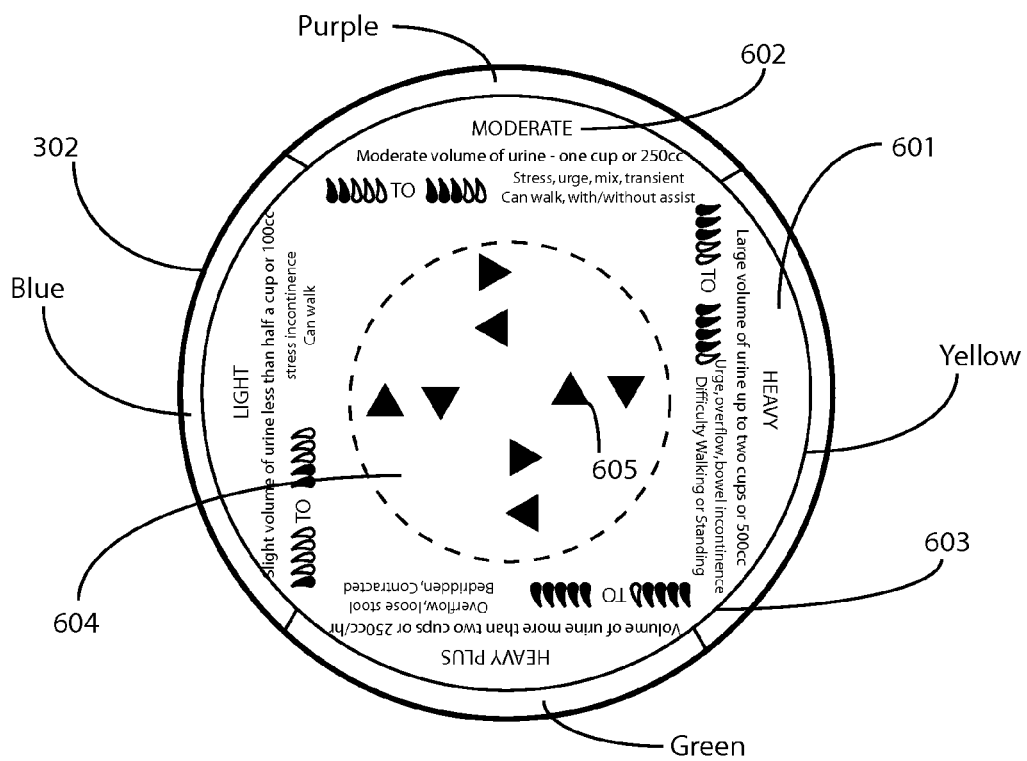
FIG. 6 illustrates one embodiment of a wheel in accordance with embodiments of the invention.

Turning now to FIGS. 5 and 6, illustrated therein is one example of an inner member 302 suitable for use in the device (300) of FIGS. 3 and 4. The inner member 302 can be made from paper, plastic, laminated paper, cardboard, or other suitable materials. In one embodiment, a first side 501 of the inner member 302 includes an outer perimeter 502 with a plurality of wearer measurements 503 disposed thereon. For example, in one embodiment the wearer measurements comprise wearer weights ranging from ninety-five pounds to two hundred and fifty pounds in five pound increments. The inner portion 504 of the first side 501 comprises a plurality of color-coded symbols 510 that are configured to be visible through an aperture of the exterior member (301) when a corresponding wearer measurement is aligned with the first wearer measurement alignment indicator (309) on the exterior member (301).

The second side 601 of the inner member 302 includes descriptions 602 of urinary output and wearer mobility on an outer portion 603 of the inner member 302. The inner portion 604 of the second side 601 comprises pointers 605 that are configured to be visible through an aperture of the exterior member (301) when a description is visible in an aperture (406) of the second side (404) of the exterior member (301).

In one embodiment, the descriptions further include graphical indicia of an amount of urinary output. For example, sets of water droplet shapes can be color-coded to indicate an amount of urinary input by coloring portions of a set blue while the others remain clear. For example, in a set of ten droplets, four may be colored blue while six remain clear. Ranges can be illustrated to, for instance by showing a set of ten droplets with four colored blue, the word "to," and another set of ten droplets with five colored blue.

Textual descriptions may be included as well. For example, "light" output may be described as "slight volume of urine less than half a cup or 100 cc." "Moderate" output can be described as "moderate volume of urine up to one cup or 2550 cc." "Heavy" output can be described as "large volume of urine up to two cups or 500 cc." "Heavy Plus" output can be described as "volume of urine more than two cups or 500 cc in four hours." Heavy Plus can further include overflow, loose stool, and other descriptors. Low mobility descriptions can include "contracted, bedridden" and "low air loss mattress." Higher mobility descriptions can include "difficulty walking or standing." Still higher mobility descriptions can include "can walk with or without assistance."

Figure 7:
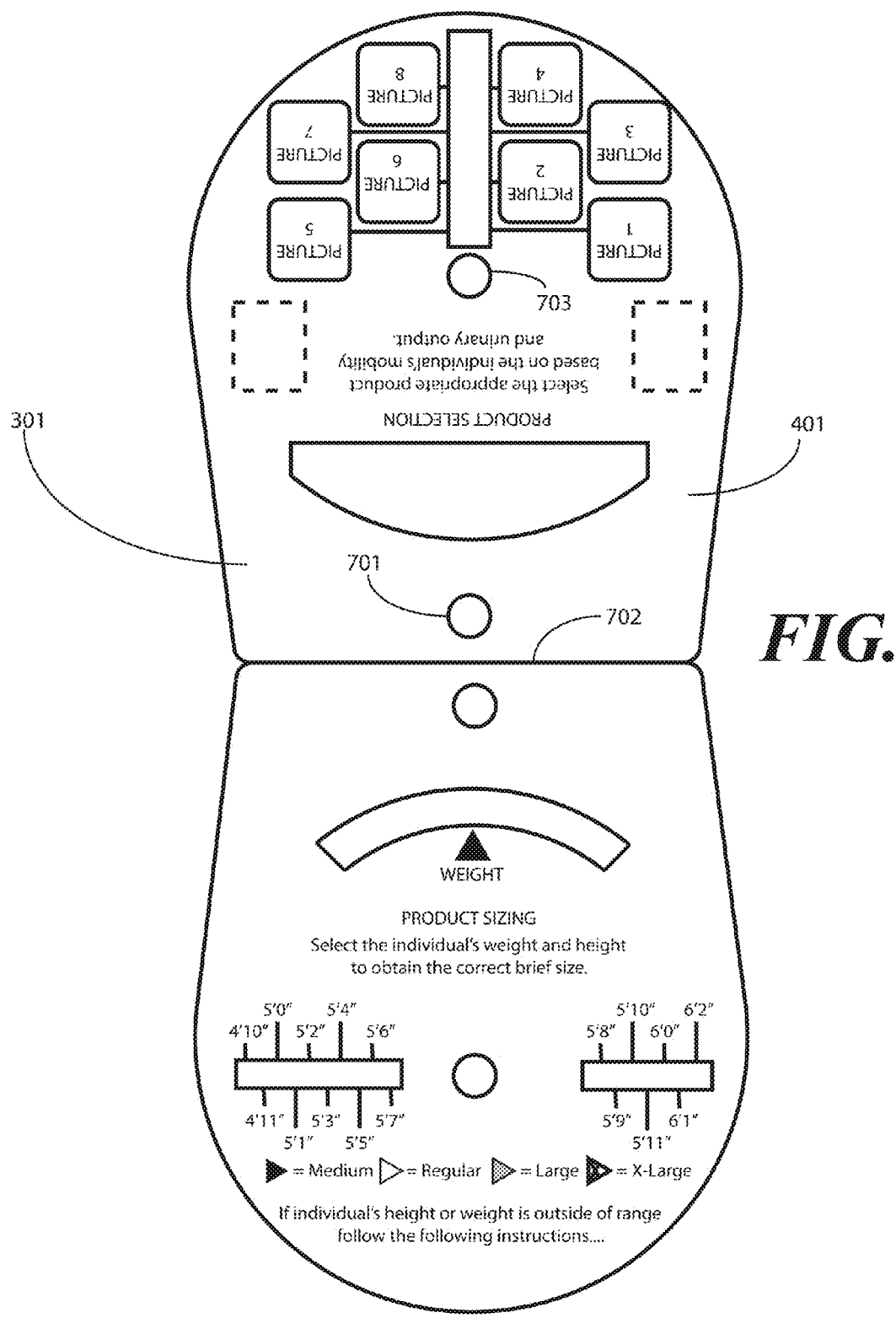
FIG. 7 illustrates one embodiment of a housing in accordance with embodiments of the invention.

Turning now to FIG. 7, illustrated therein is one example of an exterior member 301 suitable for use in the device (300) of FIGS. 3 and 4. As with the inner member (302), the exterior member 301 can be made from paper, plastic, laminated paper, cardboard, or other suitable materials. The exterior member 301 can include information disposed thereon as described with respect to FIGS. 3 and 4.

In the illustrative embodiment of FIG. 7, the exterior member 301 is configured as a unitary member with the first side 501 and second side 401 being joined at a line 702 suitable for folding. In FIG. 7, the exterior member 301 is configured with a hanging aperture 701. The hanging aperture 701 is suitable for hanging on a hook in a store room, or alternatively on a supply cart.

The exterior member 301 can be coupled to the inner member (302) of FIGS. 5 and 6 in a variety of ways. In one embodiment, a circular metal clasp passes through a coupling aperture 703 while the inner member (302) is disposed within the exterior member 301. The circular metal clasp grasps the exterior member 301 and allows the inner member (302) to pivot within the exterior member 301.

Figure 8:
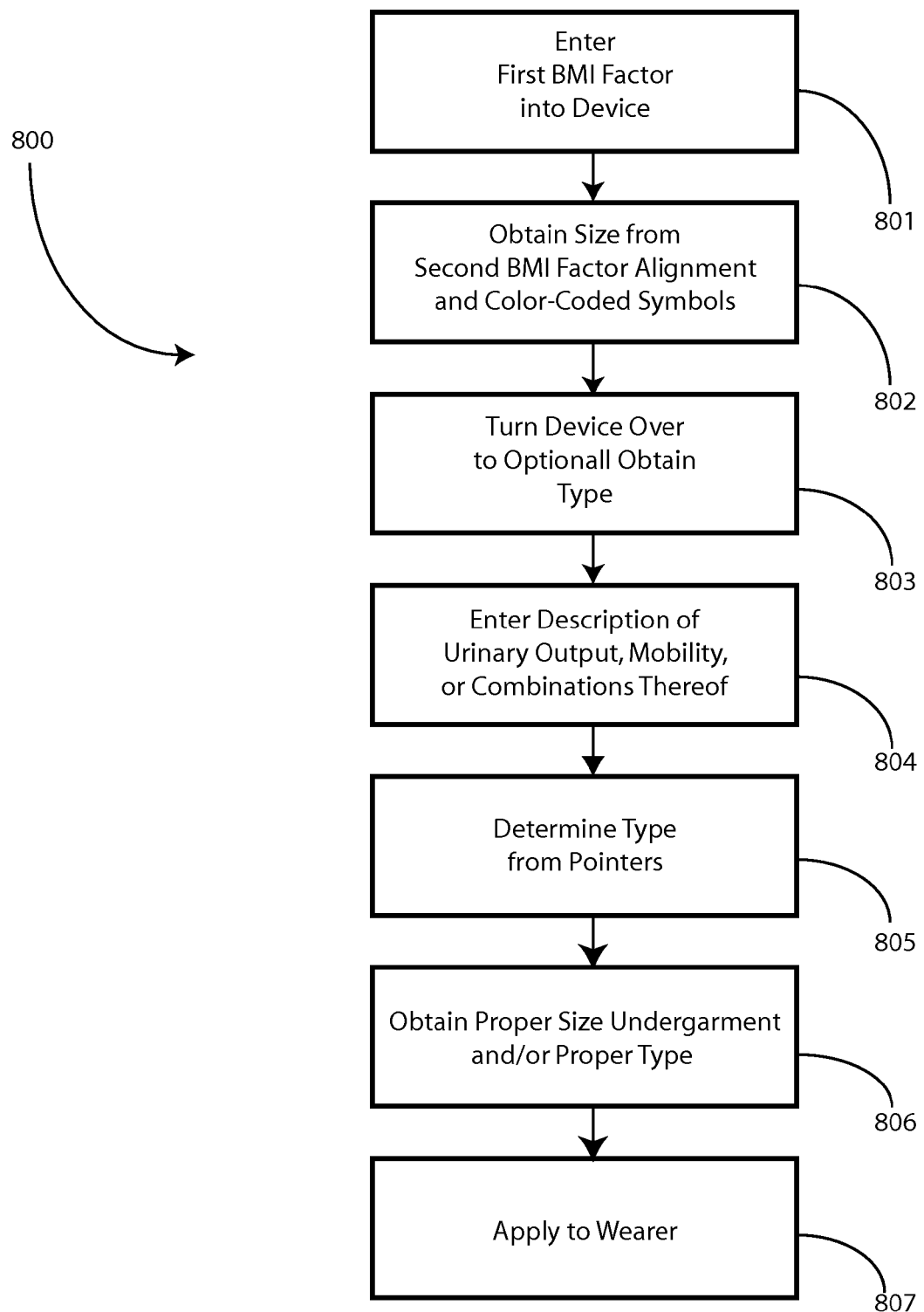
FIG. 8 illustrates a method for using a device for determining an appropriately sized medical undergarment in accordance with embodiments of the invention.

Turning now to FIG. 8, illustrated therein is one embodiment of a method 800 for using devices in accordance with the various embodiments of the invention. At step 801, a user enters a measurement corresponding to the wearer into a device for determining the appropriately sized medical undergarment. As described above, in one embodiment the measurement will be weight. However, embodiments of the invention are not so limited. Height or another measurement could be entered at this step 801. In one embodiment, step 801 is accomplished by rotating a wheel to align the first measurement with a first measurement alignment indicator as previously described.

At step 802, the user determines a size corresponding to the appropriately sized medical undergarment from a plurality of color-coded symbols aligned with a plurality of second measurements corresponding to the wearer. Specifically, the user determines—in one embodiment—which color is aligned with a second measurement alignment indicator. In one embodiment, this second measurement is the height of the prospective wearer.

At step 803, the user can optionally flip the device over to reveal the other side. Once viewing the other side, at step 804 the user can enter urinary output information corresponding to the wearer into the device for determining the appropriately sized medical undergarment. In one embodiment, this is done by rotating a wheel to present an accurate description of urinary output, wearer mobility, or combinations thereof in a window or aperture of the device.

At step 805, the user determines a type of medical undergarment to be used on the wearer based upon the information entered at step 804. In one embodiment, this is done by determining either a color of a pointer or a pictorial or textual representation of a product to which a pointer is pointing. At step 806, the user may obtain the appropriately sized undergarment. The user may then place the appropriately sized undergarment on the wearer.

It should be noted that medical undergarments, as the term is used herein, can take different forms. In one embodiment, the medical undergarments are absorbent, wearable incontinence protection devices. These devices can take many forms as well. For example, in one embodiment the undergarment can be a pad. In another embodiment, the undergarment can be a brief. In another embodiment, the undergarment can be a wrap-around covering device. In yet another embodiment, the undergarment can even comprise a sheet. Embodiments of the present invention are not to be limited in this respect.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A device for determining an appropriately sized medical undergarment, comprising:
    an exterior member having a first side and a second side, each of the first side and the second side defining at least two apertures;
    an inner member coupled to the exterior member so as to be pivotally movable within the exterior member;
    a first wearer measurement alignment indicator disposed on the exterior member adjacent to a first aperture;
    a plurality of second wearer measurement alignment indicators disposed on the exterior member adjacent to a second aperture;
    a plurality of first wearer measurements disposed about the inner member so as to be at least partially visible through the first aperture;
    a plurality of color-coded symbols disposed about the inner member so as to be at least partially visible through the second aperture, with each color representing a different size of medical undergarment;
    wherein when a first wearer measurement is aligned with the first wearer measurement alignment indicator, a corresponding plurality of color-coded sizing symbols become visibly aligned with the plurality of second wearer measurement alignment indicators, thereby indicating the appropriately sized medical undergarment for each of the plurality of second wearer measurement alignment indicators.

2. The device of claim 1, wherein the first wearer measurement comprises weight.

3. The device of claim 2, wherein the each of the plurality of second wearer measurement alignment indicators comprises a height indicator.

4. The device of claim 1, wherein the plurality of color-coded symbols comprises combinations of symbols having one of four colors.

5. The device of claim 4, wherein:
    a first color corresponds to a first size of medical undergarment;
    a second color corresponds to a second size of medical undergarment;
    a third color corresponds to a third size of medical undergarment; and
    a fourth color corresponds to a fourth size of medical undergarment.

6. The device of claim 5, wherein the first size of medical undergarment is medium, the second size of medical undergarment is regular, the third size of medical undergarment is large, and the fourth size of medical undergarment is extra-large.

7. The device of claim 5, wherein the appropriately sized medical undergarment comprises an absorbent continence care undergarment.

8. The device of claim 1, further comprising a second plurality of second wearer measurement alignment indicators disposed on the exterior member adjacent to a third aperture, wherein when the first wearer measurement is aligned with the first wearer measurement alignment indicator, a first corresponding plurality of color-coded sizing symbols become visibly aligned with the plurality of second wearer measurement alignment indicators and a second corresponding plurality of color-coded sizing symbols become visibly aligned with the second plurality of second wearer measurement alignment indicators, thereby indicating a first set of appropriately sized medical undergarments for each of the plurality of second wearer measurement alignment indicators and a second set of appropriately sized medical undergarments for each of the second plurality of second wearer measurement alignment indicators.

9. The device of claim 8, wherein the plurality of second wearer measurement alignment indicators comprise wearer height indicators, wherein the second plurality of second wearer measurement alignment indicators comprise second wearer height indicators, wherein the wearer height indicators are less than the second wearer height indicators.

10. The device of claim 1 wherein the first aperture and the second aperture are disposed along one of the first side or the second side, wherein another of the first side or the second side comprises pictorial representations of a plurality of medical undergarments disposed on the exterior member adjacent to a third aperture.

11. The device of claim 10, wherein the inner member comprises wearer discharge information disposed along the inner member so as to be visible through a fourth aperture of the another of the first side or the second side.

12. The device of claim 11, wherein when a wearer discharge description is visible within the fourth aperture, one or more pointers become visible in the third aperture, the one or more pointers identifying which of the plurality of medical undergarments are appropriate by pointing to each corresponding pictorial representation.

13. The device of claim 12, wherein the wearer discharge description comprises urinary output.

14. The device of claim 13, wherein the wearer discharge description further comprises wearer mobility information.

15. A device for determining an appropriate size medical undergarment for
a wearer, comprising:
a housing;
a wheel coupled to the housing;
one of urinary output information or wearer mobility information disposed along the wheel so as to be visible through a first aperture in the housing; and
pictorial representations of medical undergarments disposed on the housing about a second aperture in the housing;
wherein when the wheel is turned such that a selected one of urinary output information or the wearer mobility information appears in the first aperture, a corresponding one or more pointers are revealed in the second aperture to point to at least one pictorial representation of an appropriate medical undergarment.

16. The device of claim 15, further comprising a first body mass index factor alignment indicator and a plurality of second body mass index factor alignment indicators, wherein alignment of a first wearer body mass index factor with the first body mass index factor alignment indicator reveals color coded symbols indicating appropriate sizes of medical undergarments for each of the plurality of second body mass index factor alignment indicators.

17. The device of claim 15, wherein the wheel is accessible for rotation about at least a portion of a perimeter of the housing.

18. A method for determining an appropriately sized medical undergarment for a wearer, comprising:
entering a measurement corresponding to the wearer into a device for determining the appropriately sized medical undergarment;
determining a size corresponding to the appropriately sized medical undergarment from a plurality of color-coded symbols aligned with a plurality of second measurements corresponding to the wearer;
entering urinary output information corresponding to the wearer into the device for determining the appropriately sized medical undergarment; and
determining a type of medical undergarment to be used on the wearer.

19. The method of claim 18, wherein the entering the measurement corresponding to the wearer and the entering urinary output information corresponding to the wearer each comprise rotating a wheel of the device for determining the appropriately sized medical undergarment.

20. The method of claim 18, wherein the determining the type of medical undergarment comprises determining from one or more pointers aligned with one or more of a plurality of pictorial representations of different medical undergarments.

* * * * *